(12) United States Patent
Caldwell

(10) Patent No.: US 7,021,933 B2
(45) Date of Patent: Apr. 4, 2006

(54) UNIVERSAL DEPTH CUT BURR HAVING DENTAL AND SKELETAL APPLICATIONS

(76) Inventor: Mark J. Caldwell, 147 Mike Miller La., Clinton, TN (US) 37716

( * ) Notice: Subject to any disclaimer, the term of this patent is extended or adjusted under 35 U.S.C. 154(b) by 305 days.

(21) Appl. No.: 10/733,632

(22) Filed: Dec. 11, 2003

(65) Prior Publication Data

US 2005/0130103 A1 Jun. 16, 2005

(51) Int. Cl.
 A61C 3/06 (2006.01)
(52) U.S. Cl. .......................... 433/165; 606/80
(58) Field of Classification Search ............... 433/165, 433/166; 408/85, 86, 222; 407/54; 606/80
See application file for complete search history.

(56) References Cited

U.S. PATENT DOCUMENTS

| | | | |
|---|---|---|---|
| 2,280,927 A | 4/1942 | Phillips | |
| 2,453,696 A | 11/1948 | Brooks | |
| 2,855,673 A * | 10/1958 | Siegfried | 433/166 |
| 2,901,826 A | 9/1959 | Kline et al. | |
| 3,101,546 A | 8/1963 | Thomas | |
| 3,309,772 A | 3/1967 | Lieb et al. | |
| 3,576,076 A | 4/1971 | Weissman | |
| 4,264,307 A * | 4/1981 | Neuwirth | 433/166 |
| 4,389,192 A | 6/1983 | Neuwirth | |
| 4,526,542 A | 7/1985 | Kochis | |
| 4,590,929 A * | 5/1986 | Klein | 606/74 |
| 4,609,352 A | 9/1986 | Riitano | |
| 4,834,655 A | 5/1989 | Kyotani | |
| 4,854,871 A | 8/1989 | Weissman | |
| 4,992,049 A * | 2/1991 | Weissman | 433/215 |
| 5,100,322 A | 3/1992 | Weissman | |
| 5,201,619 A * | 4/1993 | Yodoshi | 409/132 |
| 5,403,187 A | 4/1995 | Wauchope | |
| 5,575,650 A | 11/1996 | Niznick et al. | |
| 5,839,897 A | 11/1998 | Bordes | |
| 5,868,572 A | 2/1999 | Lazzara et al. | |
| 5,890,897 A | 4/1999 | Kruger et al. | |
| 5,971,758 A | 10/1999 | Hugo et al. | |
| 6,186,788 B1 * | 2/2001 | Massad | 433/165 |
| 6,235,035 B1 | 5/2001 | Boukhris | |
| 6,319,005 B1 | 11/2001 | Hollander et al. | |
| 6,511,322 B1 | 1/2003 | Kometas | |
| 6,739,872 B1 * | 5/2004 | Turri | 433/75 |

* cited by examiner

*Primary Examiner*—Ralph A. Lewis
(74) *Attorney, Agent, or Firm*—Pitts & Brittian, P.C.

(57) ABSTRACT

A reduction burr for universal application for depth reduction of dental or ossiferous surfaces includes a shank of a first diameter extended to a chamfered rim angled radially inwardly to a smaller second diameter. A curved shoulder extended from the chamfered rim decreases in cross-sectional diameter to a distal end having a third diameter. A burr end having an abrasive surface thereon is extended from a junction with the shoulder distal end to a distal burr end, with the abrasive surface having sufficient hardness to cut enamel or ossiferous surfaces. The junction defines a precise stop for self-limiting the burr penetration depth into the enamel or ossiferous surfaces due to the greater second diameter of the curved shoulder contacting against adjacent uncut surfaces. A method of size reduction is disclosed for universal application of a reduction burr to precisely reduce enamel or ossiferous surfaces in both lateral and longitudinal directions.

20 Claims, 8 Drawing Sheets

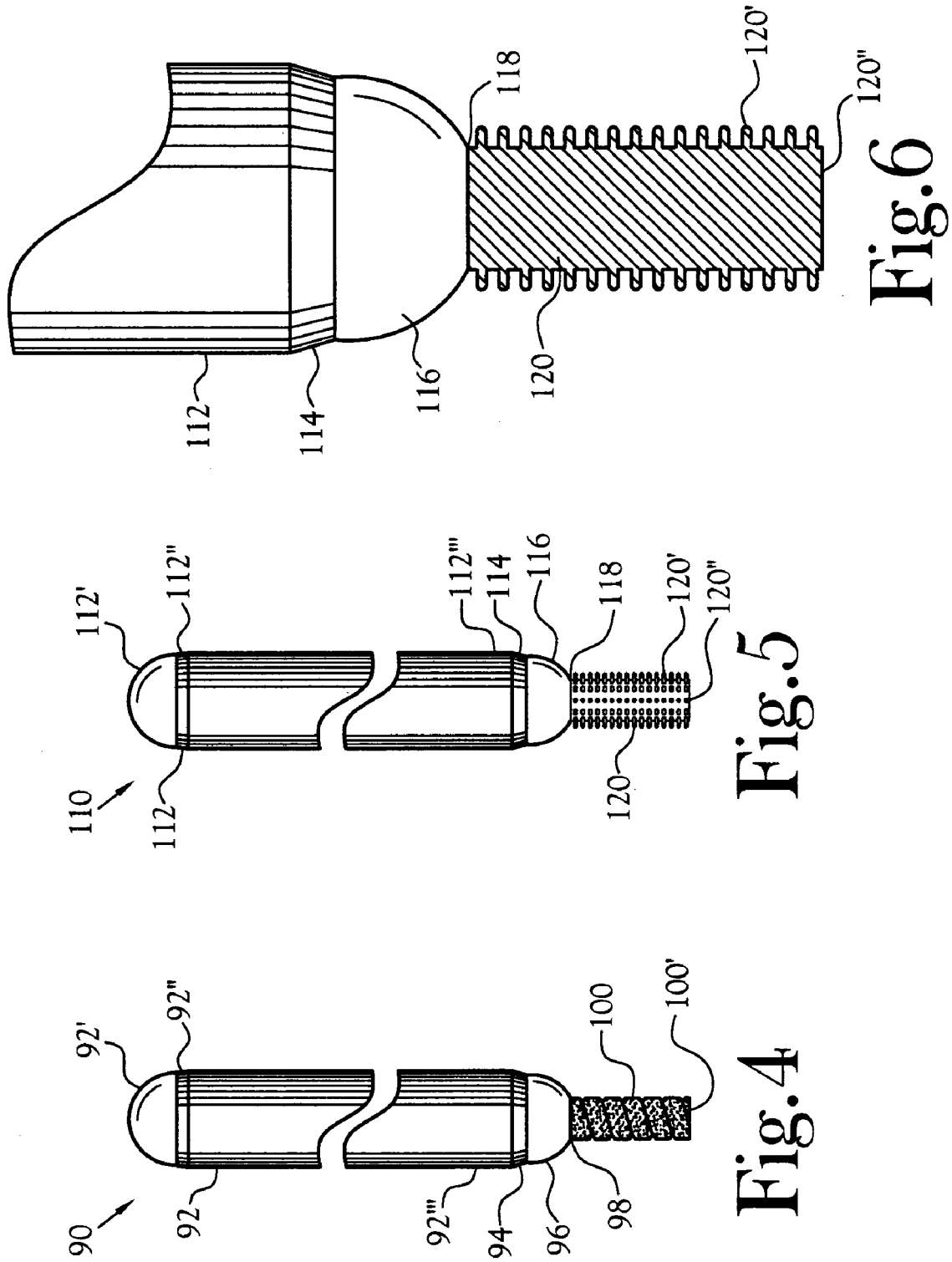

UNIVERSAL DEPTH CUT BURR HAVING DENTAL AND SKELETAL APPLICATIONS

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to cutting devices for use in dental and orthopedic applications. More particularly, this invention pertains to a universal depth cut burr for use in shaping dental surfaces and/or skeletal surfaces, and methods of application thereof.

2. Description of the Related Art

In the fields of dentistry and orthopedic medicine, precise cutting and shaping instruments are frequently utilized such as drill bits and rotary cutting tools. For dental reduction and joint repair applications, efficient and compact cutting surfaces are required for drill bits and rotary cutting tools, which are referred to hereinafter as a cutting burr or a reduction burr. A cutting burr or reduction burr must provide a precise cut having a preferred width, length, and an exact depth of penetration for removal of material from surface(s) requiring reshaping. The exact depth of penetration is typically measured in 0.5 mm or 1 mm increments, which are not readily discerned by a practitioner's eye and hand coordination without mechanical assistance. A self-limiting cutting feature is preferred for limiting the depth of penetration and cutting in order to minimize removal of excess enamel or bone material. It is preferred practice to leave as much healthy enamel surface or bone surface as possible for bonding crowns or bone grafts thereto. A precise depth of penetration also protects underlying dentin, nerves and cell tissue.

In the field of dentistry, a frequently performed dental procedure includes the shaping and reduction of enamel on crown surfaces and lateral surfaces, either dentilingual or dentibuccal, of a decayed or cracked tooth. The operating space provided within a patient's mouth is extremely limited, and minimal changes in the tooth surfaces is preferred when reducing the enamel surfaces for bonding of a gold, porcelain, or ceramic cap thereon. For shaping of dental surfaces, a reduction burr is utilized that is elongated and presents a distal cutting surface that is rotated at high speeds of about 30,000 rpm while being positioned against the appropriate dental surfaces for reduction of the appropriate lateral and occlusal surfaces of the patient's tooth.

As in dentistry, the field of gnathoplasty requires precise cutting depth instruments are required for reconstructive surgery on a patient's jaw. Further, the field of orthopedics requires precise cutting depth instruments for shaping osseous surfaces in order to partially cut, elongate, and/or shape a patient's mandible, humerus, femur, tibia and fibula, or to reconstruct a patient's joint. Numerous prior designs have attempted to indicate the depth of penetration of the cutting or abrasive surface of a reduction burr by having depth indicia imbedded in the side of the burr. Unfortunately, if the operator of the reduction burr applies undue pressure on the shank of the burr, the working surface of the burr will readily penetrate past the preferred depth thereby cutting through additional enamel or bone, with a risk of cutting into internal tissue and nerves.

Typical of the prior art is a self-limiting occlusal surface reduction burr that includes a shank extended to a burr end, and having an intermediate conical flange of a diameter significantly greater than the diameter of the shank and burr end. Additional prior reduction burrs have an intermediate positioned flange that is typically triangular or rectangular in cross-section, and the depth of cut is determined by the distance between the burr end and the outer circumference of the intermediate positioned flange which rotates in unison with the burr end. Use of a reduction burr having an intermediate positioned flange of conical, triangular or rectangular cross-section is inherently limited to cutting applications against occlusal dental surfaces lacking steep cusps due to the increased cross-sectional width of the conical, triangular or rectangular flange. The width of an intermediate flange denies seating between steeply sloped cusps, denies seating on molar inclines, and denies insertion laterally between adjacent teeth while potentially cutting the adjacent tooth surface. Further, the outer circumference of a conical, triangular or rectangular flange will lacerate the gum tissue when the occlusal reduction burr is positioned at the gingival margins of a tooth. In addition, the width of the conical, triangular or rectangular flange is not utilizable against convoluted joint surfaces having limited widths therebetween. The dentist or orthopedic surgeon must frequently change to an elongated reduction burr bit having generally straight lateral sides without an intermediate flange to produce reduction cuts along dentilingual surfaces, dentibuccal surfaces and lateral surfaces between adjacent teeth, or for producing rows of cuts along ossiferous surfaces proximal of convoluted joint surfaces. Frequent changing of reduction burr bits between ones having intermediate flanges and bits having generally straight sides is time consuming, requires unpleasant inactive periods for the patient, and increases a risk of selection of reduction burr bits having inappropriate cutting depths other than the target depth of reduction. Further, if the perimeter of an intermediate flange, whether conical, triangular or rectangular in cross-section, is not perfectly concentric, then the rotational balance of the burr bit is disturbed with creation of vibration and wobble in the distal burr bit when rotated at 30,000 rpm or higher rpm. If vibration and wobble is present but not visible to the dentist or orthopedist, the vibration transmitted through the burr end can create fractures in the tooth enamel or in the ossiferous surfaces. A preferred method for reduction of dental or ossiferous surfaces is to operate a universal reduction burr having a configuration of a minimal diameter and providing a self-limiting depth of reduction of an abrasive burr end in order to reduce the shape of any sloped crown surface and lateral dental surface, or to cut into any convoluted ossiferous surface.

Prior reduction burrs typically include a depth limiting flange disposed perpendicular to the shank and perpendicular to the working surface of the burr end. A limitation to the use of a burr having a perpendicular flange is that the burr is not easily maintained in a level orientation when moved along the patient's convoluted lateral dental surfaces, therefore generating grooves in the enamel surface having uneven depths. Further, prior reduction burrs having perpendicular flanges of significantly larger diameter relative to the shank diameter and burr end diameter can easily obstruct the dental practitioner's view of the burr end during manipulation of a drill within the patient's mouth. Intermittent obstruction of a burr end during application against a dental surface by a significantly larger diameter perpendicular flange leads to mistakes in achieving optimal reduction depths for convoluted dental surfaces. Precise cuts with limited removal of enamel is preferred in order to minimally disrupt the remaining enamel surfaces.

A universal depth cut burr is needed that is sized to be rotatably connected to a dental drill and includes an abrasive burr end for cutting and shaping each enamel surface of a patient's crown and all lateral surfaces extended above the patient's gums. A universal depth cut burr is also needed that includes a burr end junction of a lesser diameter than an adjacent rounded shoulder for providing a self-limiting depth of penetration and providing unobstructed viewing of the burr end during reduction of any crown or lateral dental surfaces. A method of reduction is also needed for shaping any convoluted dental surface or convoluted ossiferous surface by utilization of a universal depth cut burr having a self-limiting junction of a minimal diameter disposed proximal of the burr end.

BRIEF SUMMARY OF THE INVENTION

According to one embodiment of the present invention, a universal depth cut burr having a self-limiting depth of penetration is provided for reducing and shaping a crown or lateral portion of a patient's dental surfaces. The reduction burr includes a shank including a first end releasably connectable to a dental drill, an elongated body having a first diameter, and a shank second end having a chamfered rim angled radially inwardly to a second diameter that is less than the first diameter of the shank. A curved shoulder extends from the chamfered rim in a uniformly decreasing cross-sectional diameter to a distal end forming a junction having a circular cross-section of a lesser third diameter. The chamfered rim and curved shoulder have a diminishing diameter than the rotatable shank for viewing along the lengthwise axis to readily observe an abrasive burr end extended from the junction and utilized for reduction of crown and/or lateral dental surfaces for fitting an artificial crown thereon.

The abrasive burr end is rigidly joined at the junction and includes a selected length having a cylindrical cross-section extended to a distal burr end. The burr length and distal burr end includes an abrasive exterior surface of sufficient hardness to cut tooth enamel. The burr junction defines a stop of minimal diameter for providing a self-limiting depth of penetration of the burr length and distal burr end into the patient's tooth enamel during shank rotation. The curved shoulder and the junction are positioned to be in contact against adjacent tooth surfaces during rotation of the burr, thereby limiting the depth of penetration of the burr length and burr end for reducing and shaping selected dental surfaces of the patient's crown and lateral dental surfaces of any maxillary or mandibular tooth.

Another embodiment provides a universal orthopedic joint depth cut burr including an abrasive burr end having a self-limiting depth of penetration for application in reducing and shaping a convoluted bone surface. The burr includes a shank end releasably connectable to a drill, an elongated cylinder having a first diameter, and a shank second end having a chamfered rim angled radially inwardly to a lesser second diameter. A curved shoulder is extended from the chamfered rim in a uniformly decreasing cross-sectional diameter extending to a distal end forming a junction having a circular cross-section of a lesser third diameter than the chamfered rim. The curved shoulder and chamfered rim are aligned axially with the axis of the shank for balanced rotation thereof.

An abrasive burr end is rigidly joined at the junction and includes a selected length having a cylindrical cross-section extended to a distal burr end. The burr length and distal burr end includes an abrasive exterior surface of sufficient hardness to provide precise cuts in convoluted exterior surfaces of skeletal bone. The burr junction defines a stop providing a self-limiting depth of penetration of the burr length and distal burr end into the convoluted surfaces of skeletal bone during shank rotation. The curved shoulder and the lesser diameter of the junction are readily positioned in contact against adjacent uncut bone surfaces during rotation of the shank and burr end, thereby precisely self-limiting the depth of penetration to the selected length of the burr end, while allowing unhindered viewing along the length of the shank and burr end during a method of size reduction of convoluted exterior bone surfaces proximal of joint surfaces.

BRIEF DESCRIPTION OF THE SEVERAL VIEWS OF THE DRAWINGS

The above-mentioned features of the invention will become more clearly understood from the following detailed description of the invention read together with the drawings in which:

FIG. 4 is a side view of an alternative embodiment of FIG. 3A, illustrating a spiral convoluted abrasive burr end;

FIG. 5 is a side view of an alternative embodiment of FIG. 3A, illustrating an abrasive burr end having a cross-cut fissure surface;

FIG. 6 is an exploded side view of FIG. 5 illustrating a plurality of cross-cut fissure disposed along the length of the abrasive burr end;

DETAILED DESCRIPTION OF THE INVENTION

Figure 1A:
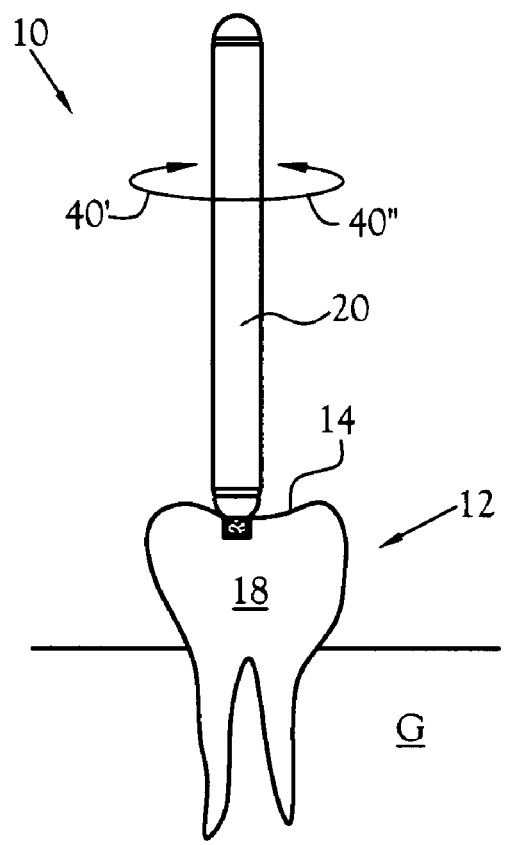
FIG. 1A is a side view of a reduction burr of the present invention for reducing and shaping a patient's dental surface.
Figure 1B:
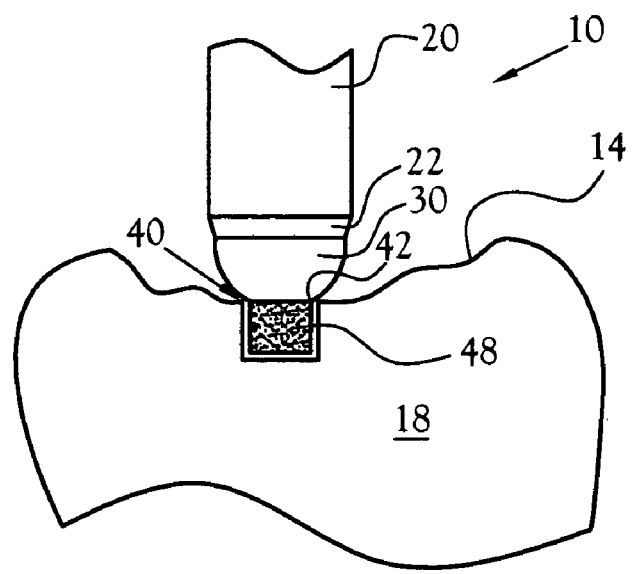
FIG. 1B is an enlarged side view of FIG. 1A, illustrating an abrasive surface of the burr end cutting a groove into the dental surface with a self-limiting curved shoulder and junction disposed against adjacent dental surfaces.

In accordance with the present invention, a reduction burr 10 is disclosed that provides a self-limiting stop mechanism for limiting the depth of penetration of the burr abrasive surfaces during cutting and reduction of a patient's dental surfaces of a tooth 12 (see FIGS. 1A and 1B). The reduction burr 10 is universally applied to readily reduce all dental surfaces requiring fabrication during tooth restoration, including the crown surface 14, also identified herein as the occlusal surface, the lingual side surface (tongue side) 16, the buccal side surface (cheek side) 18, and either or both lateral surfaces extended between the lingual and buccal side surfaces and disposed proximal of adjacent teeth 12", 12'". The reduction burr 10 disclosed herein is highly maneuverable and positionable to provide precise cuts 50, lateral grooves 58, and precise surface reductions for all tooth surfaces 12 disposed above the patient's gingival epithelium (gums) G.

Figure 2A:
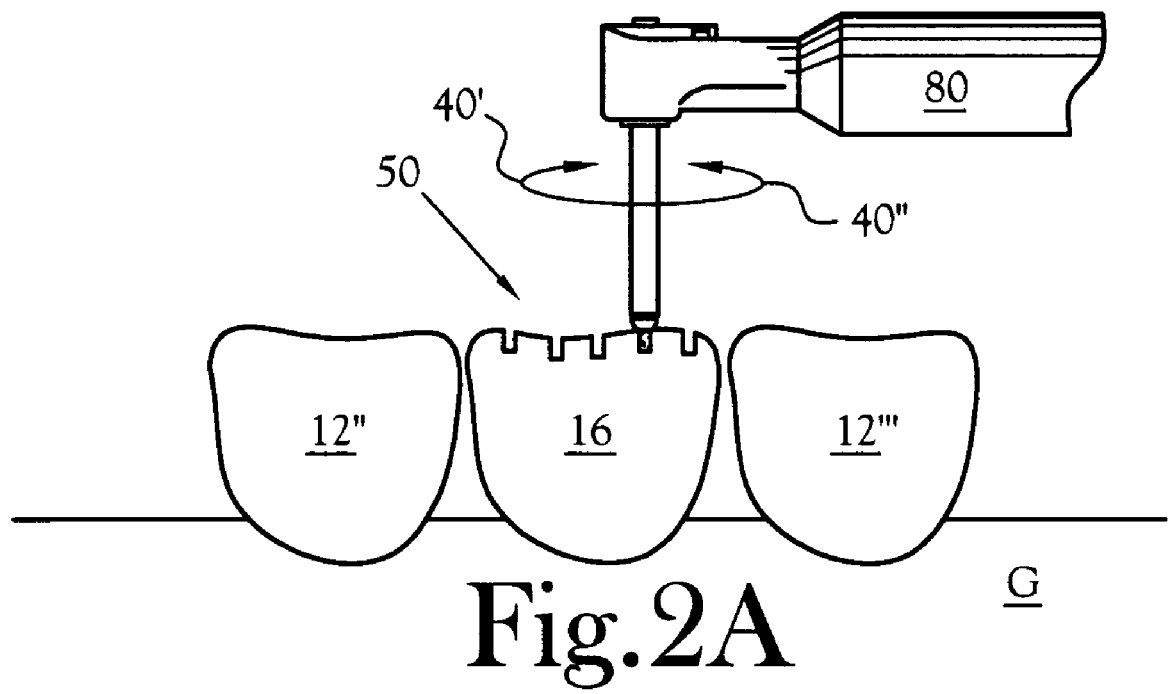
FIG. 2A is a lingual side view of a plurality of grooves cut into the dental surface to a depth limited by the curved shoulder and junction configuration of the reduction burr.
Figure 2B:
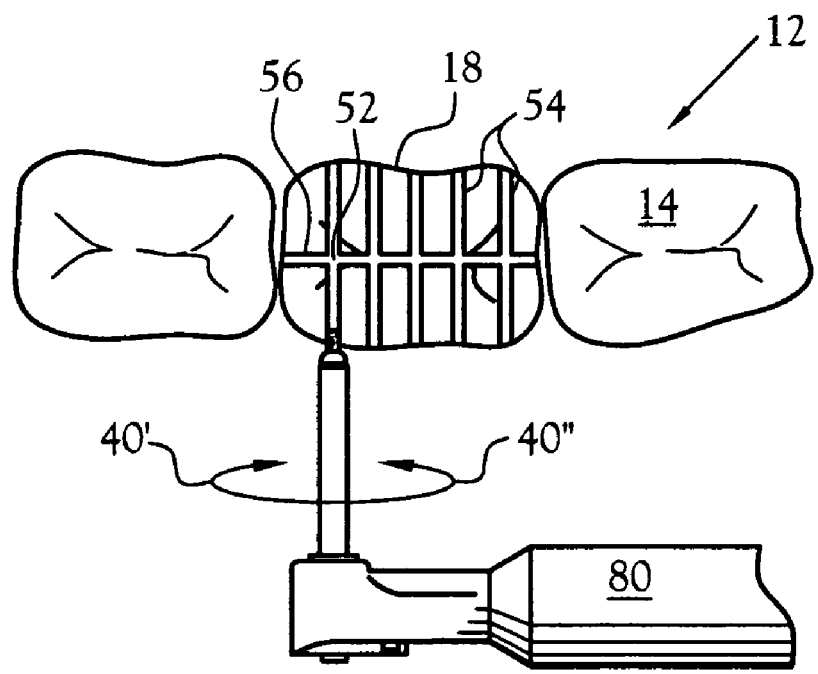
FIG. 2B is a top view of a plurality of grooves cut into the dental surface with at least one groove cut along the lingual and/or the buccal side of the tooth.
Figure 2C:
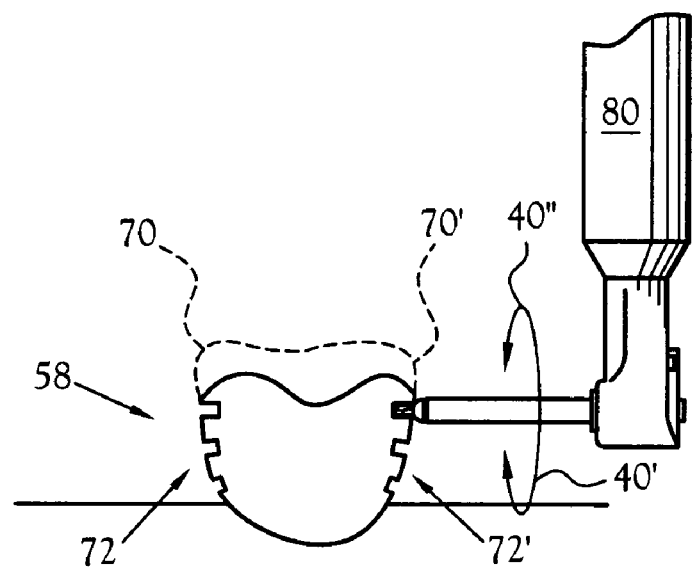
FIG. 2C is a side view of a plurality of laterally disposed grooves cut into a tooth having the crown reduced to a selected height.
Figure 2D:
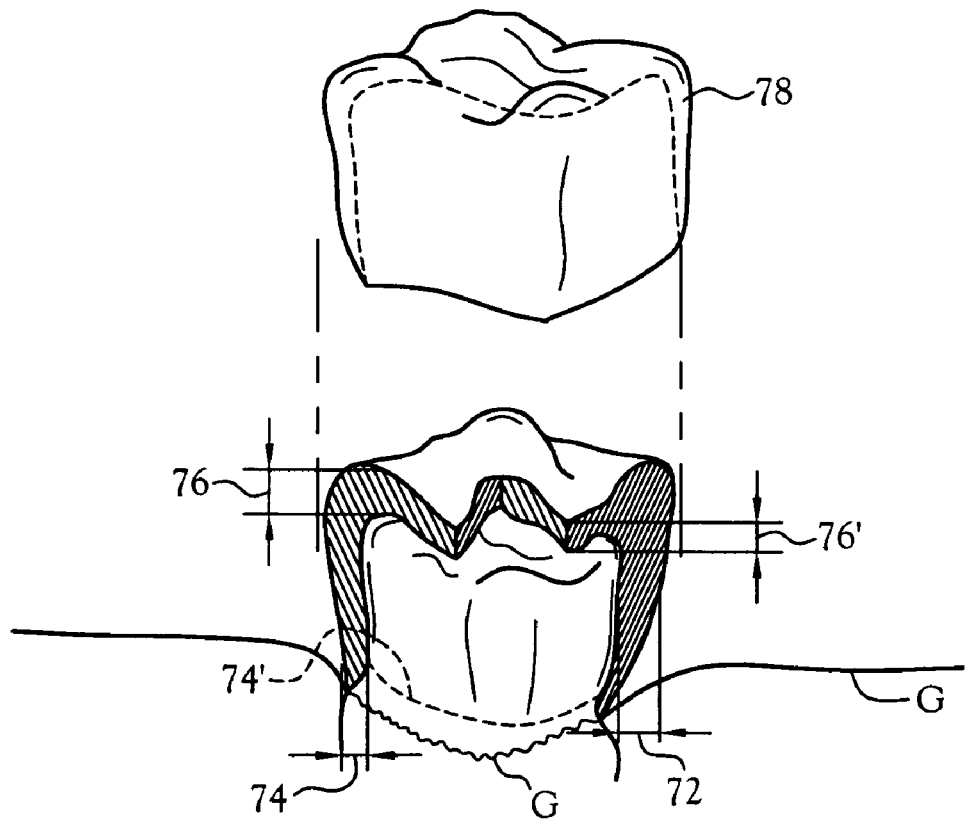
FIG. 2D is a side perspective view of dental surfaces reduced using the burr of the present invention, with an artificial cap positionable for bonding over the reduced surfaces of the crown and lateral sides of the dental surfaces.

The self-limiting depth of penetration provided by the reduction burr 10 is particularly useful for performing precise depth cuts 50, 54, 56 oriented laterally and intersecting 52 along the convoluted crown surface 14, and for performing precise depth cuts 58, 72, 74 along side dental surfaces 16, 18 (see FIGS. 2A–2C) that are adequately reduced 76, 76' in size for restorative fitting with an overlaying gold, porcelain, or ceramic crown 78 (see FIG. 2D). Specifically, the reduction burr 10 includes a self-limiting depth stop junction 42 that is disposed a selected body length 46 from a distal end 44 of a cutting burr 40. The stop junction 42 and cutting burr 40 are rotated 40', 40" at 30,000 rpm or higher rpm during application against targeted dental surfaces, thereby generating cuts 50 and grooves 54, 56, 58 of precise depths in the convoluted surfaces along the crown surface 14, the lingual side surface 16, the buccal side surface 18, and each posterior and anterior lateral surface proximal to adjacent teeth 12", 12'".

Figure 3A:
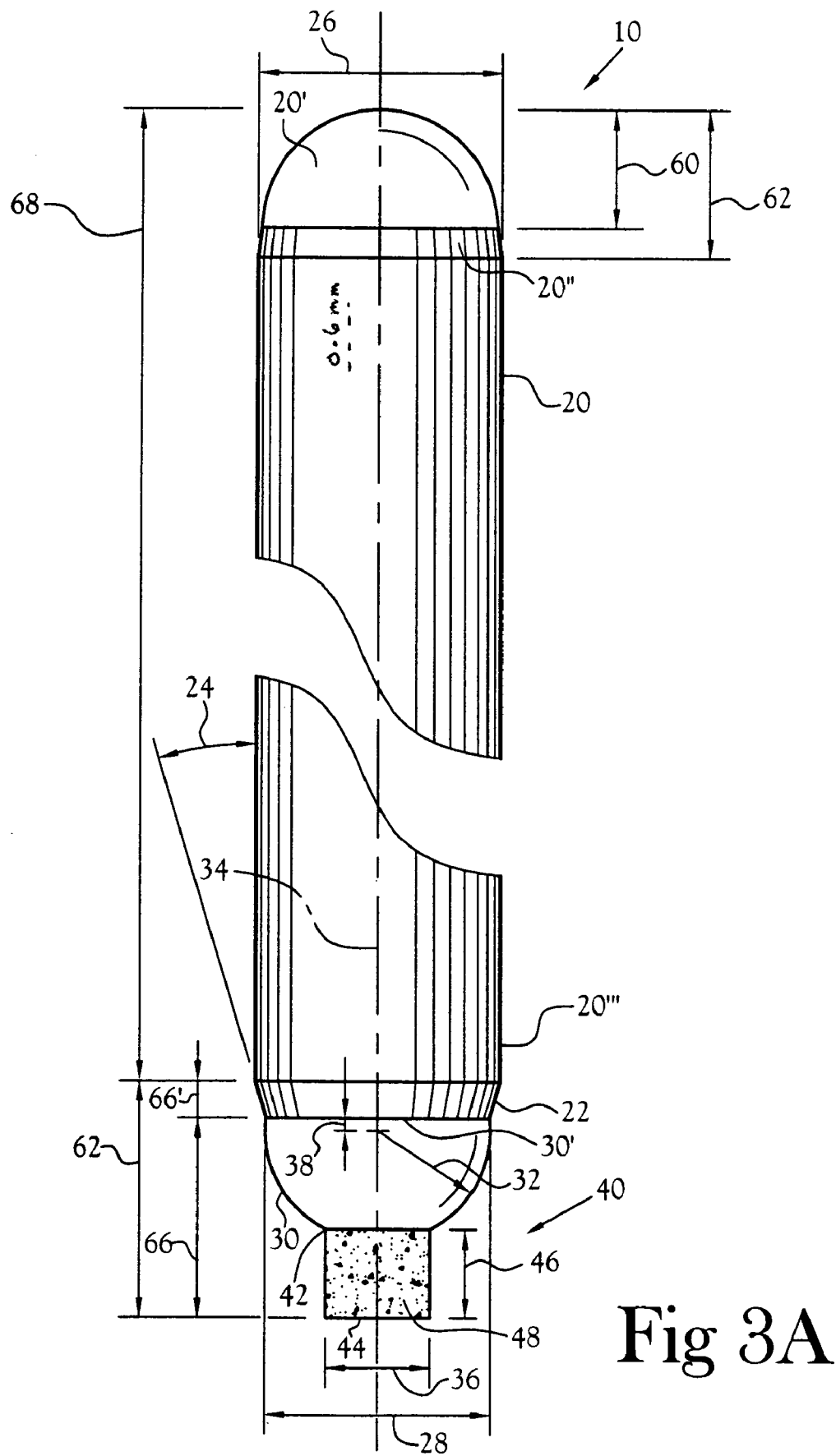
FIG. 3A is an enlarged side view of the reduction burr of FIG. 1A.

As illustrated in FIG. 3A, the reduction burr 10 of the present invention includes a shank 20 having a first end 20' that is curved outwardly with a radius 60 of between about 0.5 mm to about 1.0 mm. One preferred radius 60 is about 0.8 mm extended from a longitudinal axis 34 of the shank 20. The length and diameter of the elongated shank 20 is symmetrical about the longitudinal axis 34 to allow for balanced rotation of the shank 20 at high speeds when inserted into a dental drill 80. The first end 20' includes a recessed rim or an angled notch segment 20" having a width of about 0.20 mm, and ending about 1.0 mm 62 from the outward curved surface of the first end 20'. The angled notch segment 20" is utilized to facilitate secured connection within a female socket of a device for rotating the shank 20 such as a dental drill 80. The shank 20 further includes a substantially elongated body portion having a length 68 of about 15 mm to about 18 mm, and preferably about 16.4 mm in length 68 extended to a chamfered rim 22. The shank 20 is generally circular in cross-section in the illustrated embodiment, although other cross-sections are within the scope of the invention, such as a multi-sided shape of a hexagonal or octagonal cross-section. For a cylindrical shank 20, a first diameter 26 is selected from a range of about 1.6 mm to about 1.8 mm, with a preferred first diameter 26 of about 1.65 mm, which is maintained along the length of the elongated shank 20 from about the first end 20' to a second end 20'", on which the chamfered rim 22 is formed. One skilled in the art will recognize that any one of a variety of diameters for the shank 20 can be utilized, ranging between about 1.5 mm to about 2.0 mm for the first diameter 26. Further, one skilled in the art will recognize that alternate lengths for the shank 20 are readily utilized, ranging from about 14 mm to about 20 mm for the shank length extended from the first end 20' to the second end 20'" proximal of the chamfered rim 22. In addition, the shank 20 can include one or a plurality of markings or etchings on the exterior surface which specify a burr length 46 and/or a diameter 36 of the cutting burr 40.

The chamfered rim 22 is angled radially inwards toward the shank axis 34 at an angle 24 of between about twenty degrees to about thirty degrees when measured laterally relative to the shank outer surface. Alternatively, the chamfered rim 22 is angled radially inwards at about seventy degrees to about eighty degrees relative to a vertically oriented shank lengthwise axis 34 (see FIG. 3A). The angled length 66' of the chamfered rim 22 is between about 0.2 mm to about 0.25 mm. The length 62 between the initiation of the angled chamfered rim 22 to the distal burr end 44 is between about 1.6 mm to about 3.0 mm. The second diameter 28 of the distal end of the chamfered rim 22 is between about 1.1 mm to about 1.5 mm, with a preferred second diameter 28 of about 1.5 mm, which is a diameter of the base 30' of a uniformly curved shoulder 30 that extends distal of the chamfered rim 22 (see FIG. 3A). The base edge 30' of the curved shoulder 30 is disposed a length 66 of between about 1.35 mm to about 2.75 mm from the distal bur end 44. The curved shoulder 30 includes a non-abrasive surface curvature having a radius 32 of between about 0.7 mm to about 0.8 mm from the shank axis 34 intersection with the chamfered rim second diameter 28, with a preferred radius 32 of about 0.75 mm. In one embodiment, the center of the radius 32 of about 0.75 mm for the curved shoulder 30 is offset 38 about 0.0047 mm from the base edge 30' of the shoulder 30 and chamfered rim 22. The offset 38 provides a brief transition of minimal curvature between the second diameter 28 of the inwardly angled chamfered rim 22, and the base edge 30' of the curved shoulder 30 and cutting burr 40, thereby improving the edge contacting against uncut enamel surfaces during rotation at about 30,000 rpm or higher rpm of the cutting burr 40 extending from the curved shoulder 30. The curved shoulder 30 includes a decreasing cross-sectional area as the shoulder 30 curves to a junction 42 having a third diameter 36 of about 0.7 mm (plus or minus about 0.01 mm), which delineates one embodiment of the diameter of the cutting burr 40. One skilled in the art will recognize that an alternative shoulder radius 32 and an alternative third diameter 36 can be utilized. Preferably, the junction 42 is clearly defined by a curvature change forming an angle greater than or approaching a perpendicular orientation for the convergence of the shoulder radius 32 at the junction 42. The shoulder 30 does not have an abrasive coating on the surface area of the curved shoulder 30 up to the junction 42. An abrasive material 48 is disposed distal of junction 42 on the curved perimeter surfaces of the cutting burr 40. The junction 42 curvature defines an effective stop mechanism for self-limiting a depth of penetration for a distal end 44 of cutting burr 40 during rotation and pressure against the enamel of a tooth 12 (see FIGS. 1A, 1B, 2A–2C).

Figure 3D:
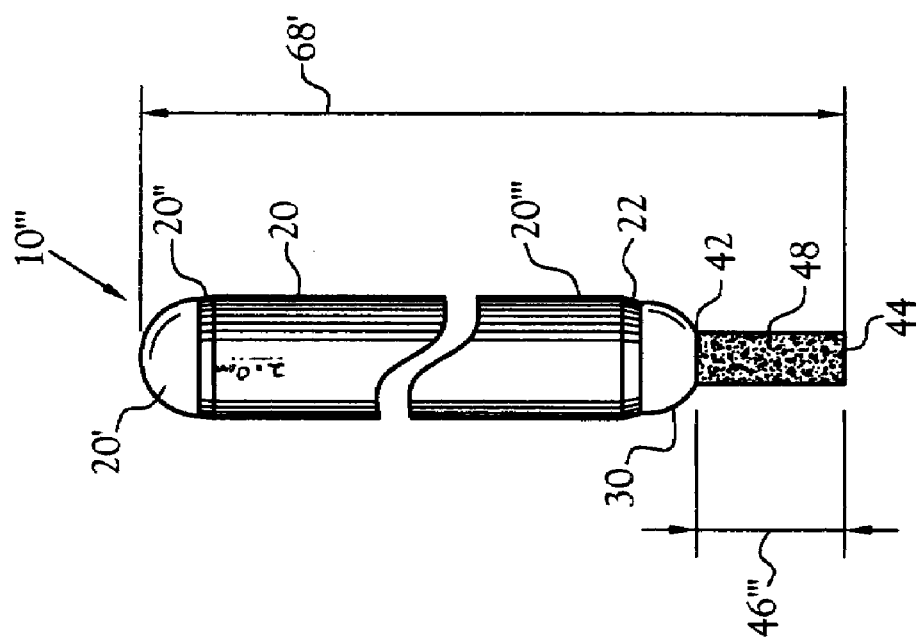
FIG. 3D is a side view of FIG. 3A having an alternative burr end length.
Figure 3C:
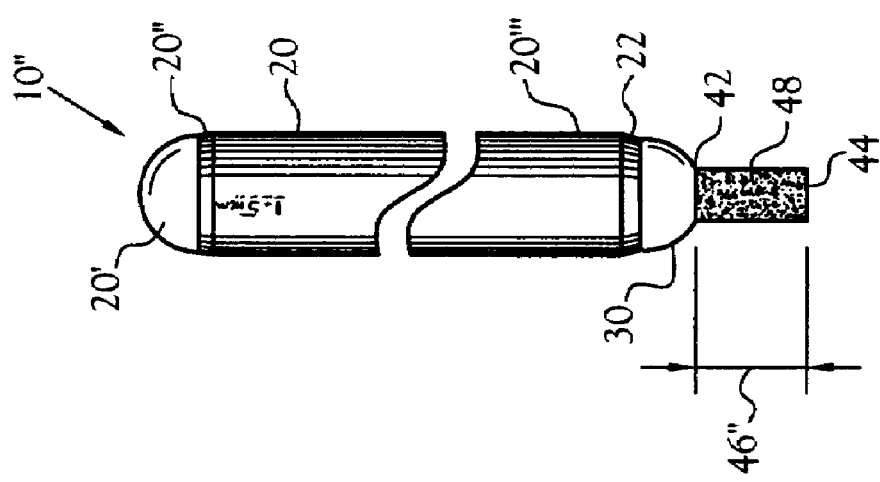
FIG. 3C is a side view of FIG. 3A having an alternative burr end length.
Figure 3B:
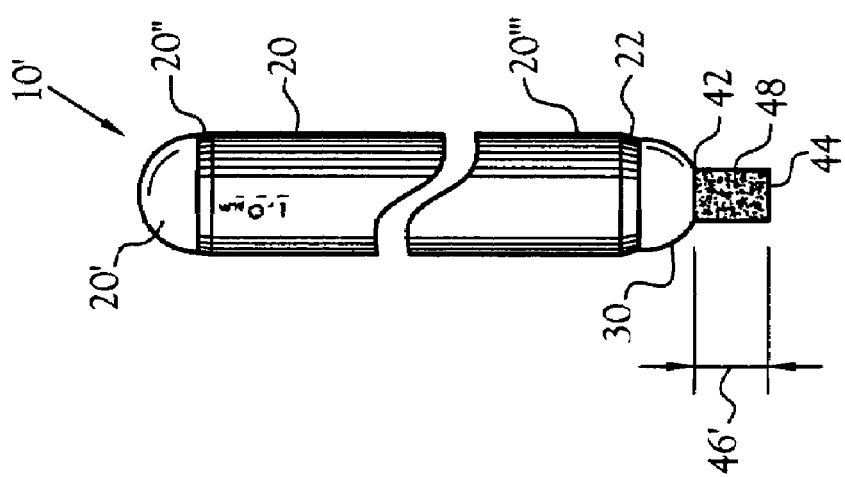
FIG. 3B is a side view of FIG. 3A having an alternative burr end length.

In one embodiment, a cylindrical cutting burr 40 includes an abrasive material 48 coating a perimeter curved surface which originates at the junction 42 and extends to a burr distal end 44. The length of the cutting bur 40 includes any of a plurality of lengths including a 0.6 mm length 46 (see FIG. 3A), a 1.0 mm length 46' (see FIG. 3B), a 1.5 mm length 46" (see FIG. 3C), or a 2.0 mm length 46'" (see FIG. 3D). The diameter of the burr distal end 44 is approximately equal to the third diameter 36 of the stop junction 42 of about 0.7 mm. One skilled in the art will recognize that any one of a variety of diameters 36 for the burr distal end 44 can be utilized, ranging from about 0.5 mm to about 0.8 mm. A cylindrical end perimeter of the burr distal end 44 includes perpendicular edges proximal of a flat distal end surface having an abrasive material coating thereon. An alternative embodiment of the burr distal end 44 can include minimally rounded distal edges (not shown). The abrasive material coating on the burr length 46 and the burr distal end 44 is preferably composed of a diamond chip coating 48 or a similar abrasive material of sufficient hardness and longevity to readily cut tooth enamel 12, or ossiferous surfaces 130 of a patient's limbs and/or mandible 150.

A method of size reduction of dental surfaces 14, 16, 18, or an ossiferous surface 130 utilizing the depth limiting burr 10 includes a plurality of steps utilized for precise reduction and shaping for a plurality of depths over the surfaces of any tooth crown 50, and for precise reduction and shaping for the lateral dental surfaces disposed above the patient's gingival epithelium (gums) G. The method of size reduction includes determining by standard dental practices the precise depth of size reduction and precise locations of size reductions required for the enamel portions of the patient's dental surfaces to allow installation of a restorative crown 78 thereon. The upper crown surface 50 can require a plurality of cutting depths for reduction of the crown corners 70, 70' and crown cuts 50, 54, 56 of between about 0.6 mm, to about 1.0 mm, and up to about 2.5 mm, due to the anatomy of each tooth and the necessary reduction required for a crown of gold, metal, and/or ceramic to fit properly over the convoluted surfaces of the dento-alveolar surface 14 and side/ lateral surfaces 16, 18. The method of size reduction further includes determining the precise depth and location of upper lateral cuts 58 and lower lateral cuts 72 required across the side portions 16, 18 of the tooth 12, including calculation of the depth and lateral length of reduction that can vary in dept between about 1.0 mm to about 1.5 mm for the upper lateral grooves 58, and/or tapering to about 1.0 mm for lower lateral cuts 72 that may be tapered in depth 74 to between about 0.5 mm or about 0.6 mm for the lingual side 16, buccal side 18, and adjacently disposed distal and medial surfaces proximal of the gums G.

The method of size reduction includes the step of selecting an appropriate burr length 46, 46', 46", 46'" of a reduction burr 10, 10', 10", 10'" for achieving the precise depth of the step of determining. Each appropriate burr end length being measured from the respective stop junction 42 between the curved shoulder 30 and the distal burr end 44 (see FIGS. 3A–3D). The method of size reduction further includes the step of manipulating the appropriated sized reduction burr 10, 10', 10", 10'" against an enamel portion of a plurality of the dental surfaces 14, 16, 18 with resulting penetration of the rotating burr end 40 being self-limiting by the stop junction 42 being disposed against adjacent uncut enamel portions. During the step of manipulating distal burr end 44, the lesser diameter 36 of the stop junction 42 and the same or lesser diameter of the distal burr end 44 allows viewing lengthwise along the shank 20, and the decreasing cross-section of the shoulder 30, for periodic viewing of the stop junction 42 and the abrasive cutting burr 40 by an operator without having to repeatedly remove the burr end 44 from the cut groove 54, 56, 58 to confirm the depth of cutting (essentially the length 46 of the cutting burr 40, during the step of manipulating and an associated step of cleaning with compressed air or a stream of water directed into the respective cuts and grooves 50, 54, 56, 58, 72, and reduced surfaces 72, 74, 76 of the tooth 12.

Figure 7:
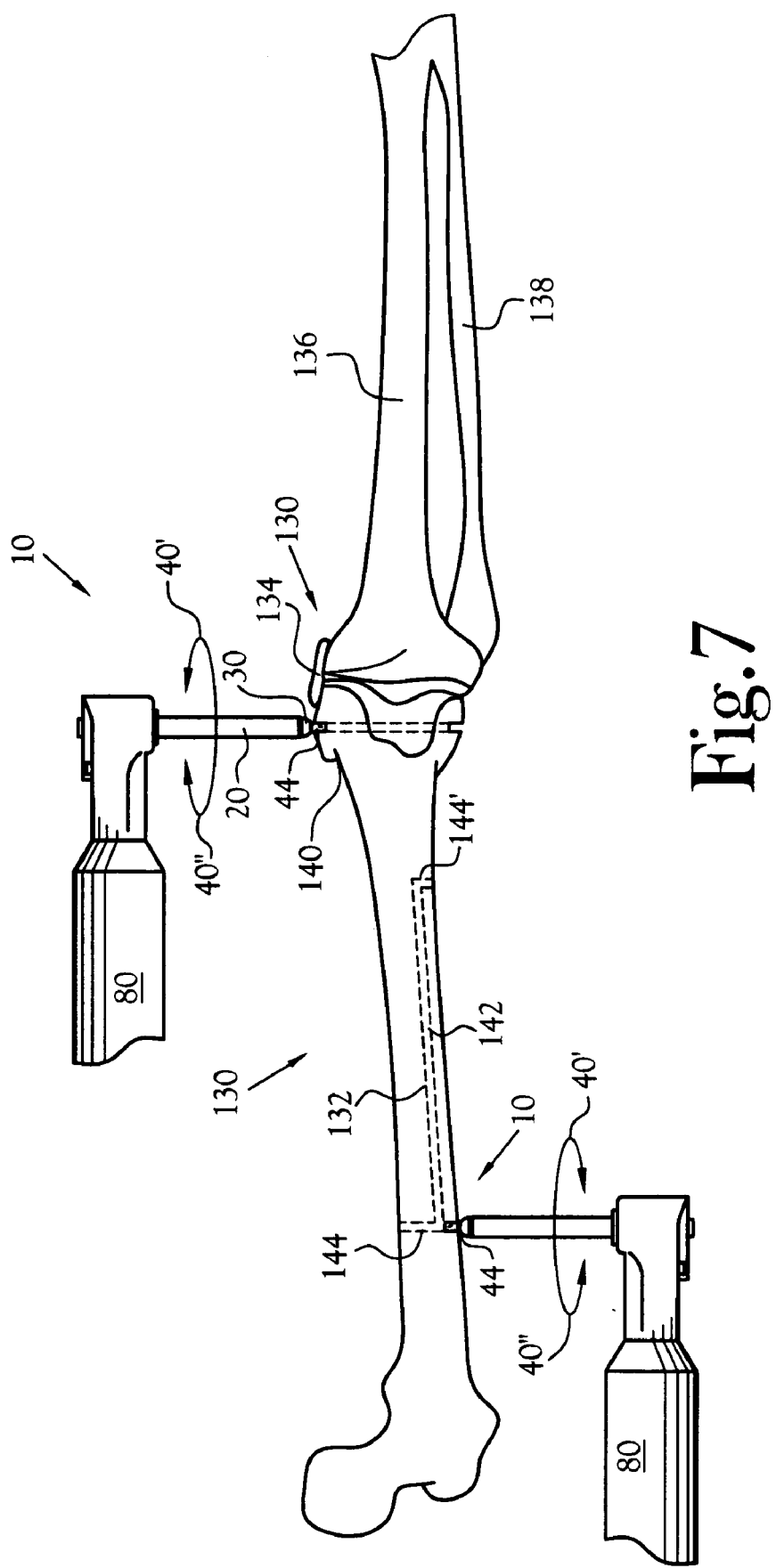
FIG. 7 is a side view of an alternative application of the reduction burr of the present invention for cutting ossiferous surfaces along a femur and proximal of a skeletal joint.

Alternative embodiments include reduction burrs 90, 110 illustrated in FIGS. 4–7, which are utilized for cutting, shaping, and reducing of tooth surfaces 12 (see FIGS. 1A, 1B and 2A–2C), and/or for cutting, shaping and reducing of ossiferous surfaces 130 proximal of, or along the surface curvature 140 of a ossiferous surface 130 proximal of a skeletal joint such as the knee and patella (see FIG. 7). A reduction burr embodiment having a self-limiting depth of penetration is illustrated in FIG. 4 and includes a reduction burr 90 having an elongated shank 92 with a rounded first end 92' extended from a perimeter angled notch 92". The shank 92 extends to a second end 92'" having a first diameter of approximately 1.65 mm, which is maintained along a shank length of between about 16 mm to about 17 mm. Distal of the second end 92'" is a chamfered rim 94 angled radially inward toward the shank axis, for rigid connection to a uniformly curved shoulder 96 of decreasing diameter and decreasing cross-sectional area as the distal end of the shoulder 96 converges to fixedly join to a junction 98 having a third diameter of about 0.7 mm. The third diameter delineates the diameter of the cutting burr 100, and is less than the second diameter of between about 1.1 mm to about 1.5 mm for the chamfered rim 94. Preferably, the junction 98 is clearly defined by a curvature change forming an angle greater than or approaching a perpendicular orientation for the convergence of the curved shoulder 96 at the junction 98. The curvature change at the junction 98 defines an effective stop mechanism for self-limiting the depth of penetration for the rotatable cutting burr 90 during application against tooth surfaces 12, or against the surface curvature 140 of ossiferous surfaces 130 proximal of a skeletal joint 130. As illustrated in FIG. 4, one embodiment of the cutting burr end 100 is a cylinder body having a cork-screw ridged surface angled laterally across the diameter of the cylinder body, and having an abrasive coating thereon, extending to a distal burr end 100', also having abrasive coating thereon. The abrasive coating can include a material having diamond chips therein, or a carbide material having ridges thereon. The abrasive coating can include similar abrasive material of sufficient hardness and longevity to readily cut tooth enamel 12 or ossiferous surfaces 130 proximal of a skeletal joint or along a length of bone.

An additional embodiment is illustrated in FIGS. 5 and 6, for a reduction burr 110 having a stop junction 118 and an alternative configuration for a distal burr end 120. A reduction burr 100 having an elongated shank 112 with a rounded first end 112' extended from a perimeter angled notch 112". The shank 112 extends to a second end 112'" having a first diameter of approximately 1.65 mm, which is maintained along a shank length of between about 16 mm to about 17 mm. Distal of the second end 112'" is a chamfered rim 114 angled radially inward toward the shank axis, for rigid connection to a uniformly curved shoulder 116 of decreasing diameter and decreasing cross-sectional area as the distal end of the shoulder 116 converges to fixedly join to a junction 118 having a third diameter of about 0.7 mm. The third diameter delineates the diameter of the cutting burr 120, and is less than the second diameter of about 1.1 mm to about 1.5 mm for the chamfered rim 114. Preferably, the junction 118 is clearly defined by a curvature change forming an angle greater than or approaching a perpendicular orientation for the convergence of the curved shoulder 116 at the junction 118. The curvature change at the junction 118 defines an effective stop mechanism for self-limiting the depth of penetration for the rotatable cutting burr 110 during application against tooth surfaces 12, or against the surface curvature 140 of an ossiferous surface 130 proximal of a skeletal joint. As illustrated in FIG. 6, an additional embodiment of the cutting burr end 120 includes a cylinder extended distal of the junction 118, and having a perimeter surface on which a plurality of cross-cut fissures 120' are disposed which form an effective surface for readily cutting, shaping and reducing tooth enamel and/or ossiferous surfaces proximal of, or within the curvature of a skeletal joint 130. The plurality of cross-cut fissures 120' are preferably composed of high strength carbide steel material, and are longitudinally aligned to extend to a distal burr end 120".

A method of utilization for the depth limiting burr 10 is disclosed, including a step of providing a reduction burr 10, 90, 110, having an appropriate shank length 68 which allows positioning the burr 10 within the confines of a patient's mouth or within an incision proximal of a skeletal joint surface. The step of providing further includes providing a shank first diameter 26 that is releasably connected within a drill 80 and mandrel for variable speed rotation 40', 40" of the burr 10. The step of providing further includes the elongated shank 112 being extended to a curved shoulder having a smaller cross-section than the elongated shank, and having a stop junction formed by a distal burr end joined to the curved shoulder. The stop junction and the distal burr end have a sufficiently lesser diameter than the cross-section of the curved shoulder to provide an angled junction that is readily positioned against adjacent enamel portions not impacted by the cutting burr 40, thereby limiting the penetration depth of the distal burr end 44 into the dental surface impacted by the cutting burr 40. A step of manipulating includes applying a rotating length of a cutting burr 40 having an abrasive material thereon against a dental surface or against ossiferous surfaces for cutting and size reduction thereof. The appropriate length 46 of the distal burr end 44 is preferred to be in the range of a 0.6 mm length 46 (see FIG. 3A), a 1.0 mm length 46' (see FIG. 3B), a 1.5 mm length 46" (see FIG. 3C), or a 2.0 mm length 46''' (see FIG. 3D). A step of cutting and reducing the enamel portion or ossiferous portion of impacted surfaces is accomplished by the distal burr end of the selected depth being manipulated in at least one dimension laterally and longitudinally along the dental surface or ossiferous surface targeted for size reduction. During the steps of manipulating and reducing, the stop junction 42 serves as a precise stop mechanism for self-limiting the depth of penetration for the rotating distal burr end 44 when applied against dental surfaces 12, or ossiferous surfaces 130.

An additional method of utilization for the depth limiting burr 10 is illustrated in FIG. 7 for application of the reduction burr 10 to produce size reduction, longitudinal cuts 142, and/or lateral cuts 144, 144' of precise depth in the ossiferous surfaces 130 along an axial length of a femur 132, tibia 136 or fibula 138 in order to lengthen. During application of the reduction burr 10 having a self-limiting junction 42 against a femur, tibia, and/or against the knee joint surfaces proximal of the patella 134, the steps of utilization are similar to the respective steps of providing, determining, selecting, manipulating and reducing the dental surfaces as provided hereinabove. A step of providing includes selecting a burr length 46 having an abrasive surface thereon of between about 0.5 mm to about 30.0 mm when the cutting burr 40 is utilized to reduce ossiferous surfaces of the patient's hand, maxillofacial area, or spinal column. The step of providing further includes a shank first diameter 26 that is increased in size to between about 2.0 mm to about 6.0 mm, due to the reinforced structural requirements for operating a reduction burr 10 utilized for a heavy orthopedic procedure on the ossiferous surfaces proximal of a shoulder, hip or knee. The burr length 46 of the abrasive surface of a cutting burr 40 utilized in heavy orthopedic procedures can include burr lengths 46 of between about 20 mm to about 50 mm. One skilled in the art will readily recognize that the method of utilization for the depth limiting reduction burr 10 can be utilized for cutting and reduction of ossiferous surfaces proximal of the patient's skeletal surfaces proximal of the ankle, knee, hip, shoulder, elbow, hand, maxillofacial area, or spinal column when combined with generally accepted surgical techniques related to skeletal reconstruction and/or joint implants.

Figure 8A:
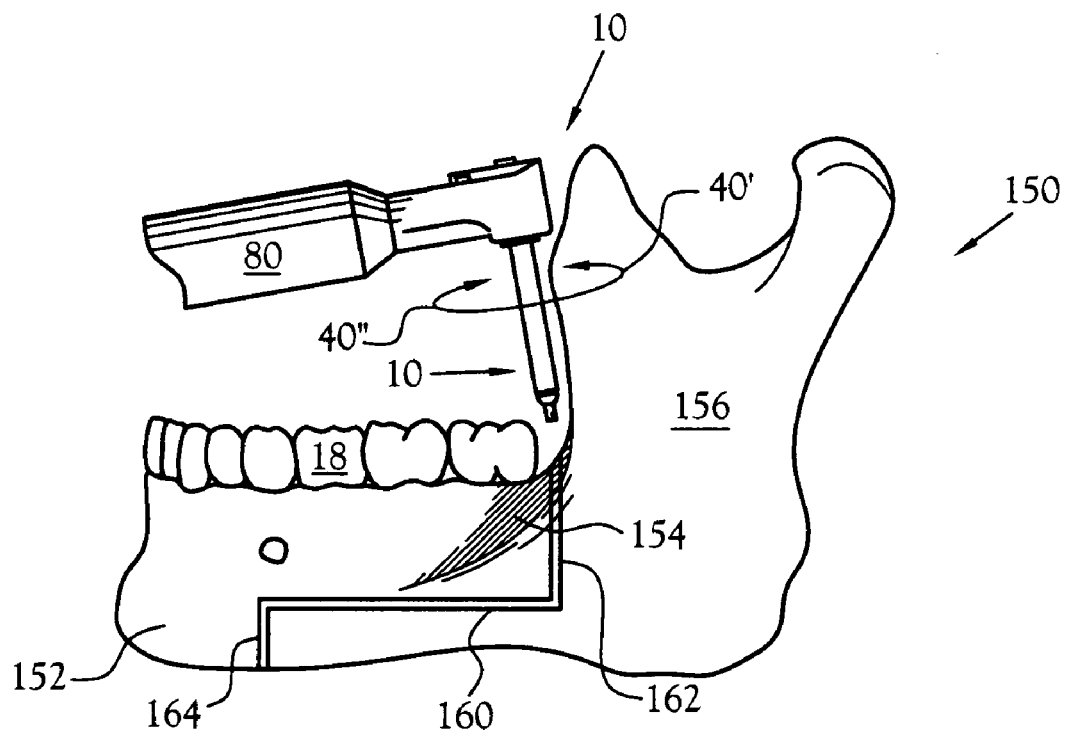
FIGS. 8A and 8B are respective exterior and interior side views of an alternative application of the reduction burr of the present invention for cutting ossiferous surfaces along a mandible.
Figure 8B:
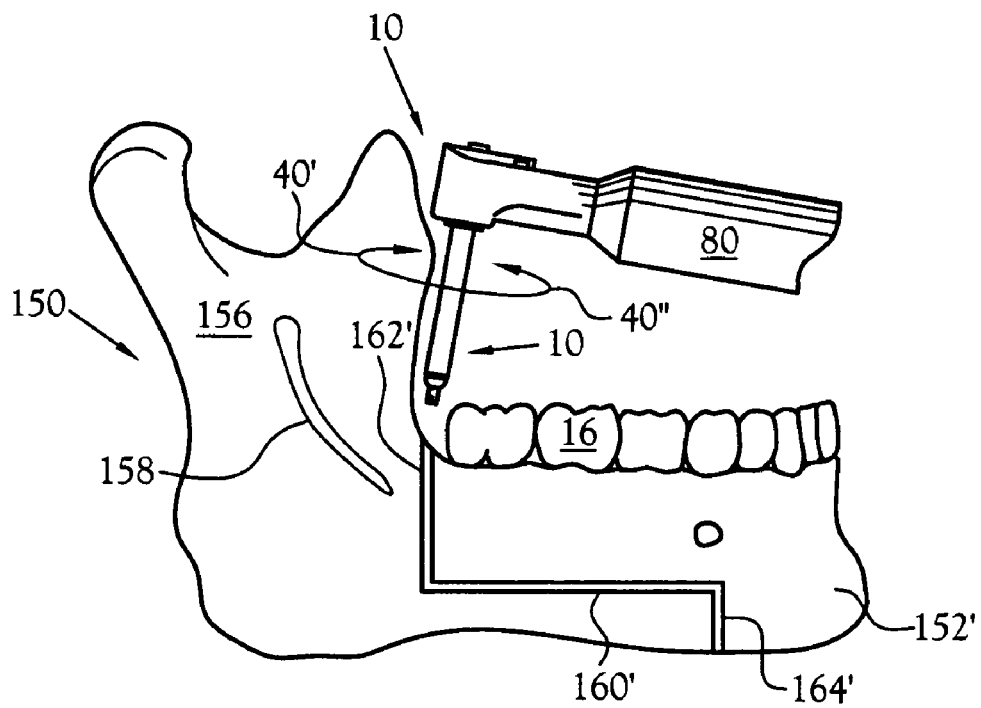

An additional method of utilization for the depth limiting burr 10 is illustrated in FIG. 8 for application of the reduction burr 10 during an osteotomy of the ossiferous surfaces 130 of a mandible 150 to lengthen the mandible to achieve proper occlusion of the patient's teeth. Precise cuts 160, 160' are required of a precise depth into the mandible surfaces of between about 0.5 mm to about 2.5 mm. The precise cuts and are extended along a patient's mandible outer body 152 and inner body 152' proximal of the outer and inner portions of the ramus 156, 156', and below the outer oblique line 154 and the inner canal 158 of the mandible 150. The method of utilization includes a step of providing a reduction burr 10, 90, 110, having an appropriate shank length 68 which allows positioning a selected body length 46 of a cutting burr 40 against the respective surfaces of the outer body 152 and inner body 152' of the mandible 150. A step of manipulating includes sequentially applying a cutting burr 40 against the surfaces of the outer body 152 and inner body 152' of the mandible 150. The rotating length of the cutting burr 40 includes a stop junction 42 and an abrasive material 48 distal of the stop junction 42, for limiting the depth of cutting through the relatively thin and varied depths of the ossiferous material of ramus 156, 156' and the mandible body 152, 152'. A step of cutting the selected ossiferous surfaces is accomplished by the distal burr end 44 and the burr length 46 of abrasive material 48 being applied into the ossiferous surface a selected depth equal to the burr length 46 distal of the stop junction 42. The step of cutting further includes progressively moving the rotating cutting burr 40 laterally and longitudinally along the ossiferous surfaces to complete formation of the required cuts, grooves, and size reduction of the ossiferous surfaces. The steps of manipulating and cutting are repeatable, with the stop junction 42 serving as a precise stop mechanism for self-limiting the depth of penetration for the rotating burr 40 along the mandible 150. After the steps of the method of utilization are accomplished for selected mandible surfaces, the outer and inner body portions 152, 152' are displaced forward relative to the outer and inner ramus portions 156, 156' for lengthening the mandible 150, while allowing sufficient overlap of surfaces adjacent the cuts 160, 162, 164 to provide adequate surface area for rigid fixation of the mandible 150 during healing after surgery.

From the foregoing description, it will be recognized by those skilled in the art that a reduction burr 10 is provided for universal application for precise cutting, shaping and reduction of all dental surfaces or ossiferous surfaces due to incorporation of an effective stop mechanism for self-limiting a depth of penetration for any length of rotatable cutting burr ends 40, 100, 120. The stop mechanism for self-limiting the depth of penetration is provided by a junction 42 being a sufficiently lesser diameter than the cross-section of the second diameter 28 of a rim 22 and curved shoulder 30, to provide an angled configuration at the junction 42 that is positioned against adjacent uncut enamel surfaces or ossiferous surfaces, thereby limiting the penetration depth of a distal burr end 44 of the reduction burr 10 into a dental surface or an ossiferous surface.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

I claim:

1. A reduction burr for shaping a patient's dental surface, comprising:
   a shank including a first end of an elongated body having a first diameter extended symmetrical about a shank axis to a second end of said shank from which a chamfered rim is angled radially inwards to a second diameter being less than said first diameter;
   a curved shoulder extended from said chamfered rim, said curved shoulder having a uniformly decreasing cross-sectional diameter extending to a distal end, said distal end having a circular cross-section being less than said second diameter of said chamfered rim, said curved shoulder and said chamfered rim being aligned axially with said shank axis for balanced rotation; and
   a burr rigidly joined at a junction with said shoulder distal end, said burr including a selected body length having a cylindrical cross-section of a third diameter extended to a burr end, said burr body length and burr end having an abrasive surface thereon of a sufficient hardness to cut tooth enamel;
   whereby said junction defines a stop for self-limiting a depth of penetration of said burr into the patient's dental surface during rotation of said shank and burr as said curved shoulder and said junction contact adjacent uncut tooth enamel, thereby said rotating burr is readily directed to reduce any selected dental surface of the patient's crown and lateral dental surfaces.

2. The reduction burr of claim 1 wherein said burr body length extended from said junction to said burr end is between about 0.5 mm to about 2.5 mm.

3. The reduction burr of claim 2 wherein said third diameter of said cylindrical cross-section of said burr is between about 0.5 mm to about 1.0 mm.

4. The reduction burr of claim 3 wherein said abrasive surface of said burr body length and burr end includes a coating of diamond powder.

5. The reduction burr of claim 3 wherein said shank includes a marking specifying said burr body length and/or said third diameter of said burr.

6. The reduction burr of claim 1 wherein said abrasive surface of said burr body length and burr end includes a carbide coating thereon and having cross-cut fissures interdisposed along said burr body length surface and burr end.

7. The reduction burr of claim 1 wherein said first diameter is between about 1.5 mm to about 2.0 mm.

8. The reduction burr of claim 1 wherein said second diameter is between about 1.1 mm to about 1.5 mm and said chamfered rim is angled radially inwards toward said shank axis at an angle between about 70 degrees to about 80 degrees.

9. The reduction burr of claim 1 wherein said curved shoulder includes a radius of between about 0.7 mm to about 0.8 mm extended from said chamfered rim second diameter.

10. A depth cut burr for shaping ossiferous surfaces of a patient's skeleton, comprising:
    a shank including a first end and an elongated body having a first diameter, said elongated body having a second end from which a chamfered rim is angled radially inwardly to a second diameter less than said first diameter;
    a curved shoulder extended from said chamfered rim, said curved shoulder having a uniformly decreasing cross-sectional diameter extending to a distal end, said distal end having a circular cross-section being less than said second diameter of said chamfered rim, said curved shoulder and said chamfered rim being aligned axially with said shank for balanced rotation; and
    a burr rigidly joined at a junction with said distal end of said curved shoulder, said burr including a selected body length extended to a distal burr end and having a cylindrical cross-section of a third diameter less than said second diameter of said chamfered rim, said burr body length and distal burr end having an abrasive surface thereon of sufficient hardness to cut ossiferous tissue;
    whereby said junction defines a stop for a self-limiting depth of penetration of said burr body length and distal burr end into the patient's ossiferous tissue during shank rotation as said curved shoulder and said junction are contacted against adjacent ossiferous surfaces thereby said burr body length and distal burr end reduces each of selected ossiferous surfaces of the patient's skeleton.

11. The depth cut burr of claim 10 wherein said selected body length of said burr from said junction to said distal burr end is selected from a range comprising a length between about 0.5 mm to about 50 mm.

12. The depth cut burr of claim 11 wherein said third diameter of said burr cylindrical cross-section is between about 0.5 mm to about 6 mm.

13. The depth cut burr of claim 12 wherein said burr body length and distal burr end are coated with diamond powder.

14. The depth cut burr of claim 12 wherein said burr body length extended to said distal burr end includes a carbide coating thereon and having cross-cut fissures interdisposed along said burr body length.

15. A method of size reduction to precise depths of enamel portions of a dental surface, comprising the steps of:
    providing a reduction burr including an elongated shank extended to a curved shoulder having a smaller cross-section than said elongated shank, and having a stop junction formed by a distal burr end joined to said curved shoulder, said stop junction and said distal burr end having a sufficiently lesser diameter than said cross-section of said curved shoulder to provide an angled junction positioned against adjacent enamel portions not impacted by said distal burr end, thereby limiting the penetration depth of said reduction burr into the dental surface impacted by said distal burr end;
    determining the precise depth of size reduction required for the enamel portions of the dental surface;

selecting an appropriate length of a burr end of said reduction burr for achieving the precise depth of said step of determining, said appropriate length being measured from said stop junction proximal of said curved shoulder to said distal burr end of said reduction burr;

manipulating said reduction burr against the enamel portions of the dental surface with resulting penetration of said reduction burr into the enamel portions being self-limiting by said stop junction disposed against adjacent enamel portions, whereby viewing by an operator of resulting penetration of said stop junction and distal burr end is readily accomplished due to said sufficiently lesser diameter of said stop junction and distal burr end; and reducing the enamel portions impacted by said burr end for said selected depth in at least one dimension laterally and longitudinally along the dental surface targeted for size reduction.

16. The method of claim 15 wherein the enamel portions of the dental surface targeted for size reduction is selected from a group consisting of a crown enamel surface, a buccal enamel surface, a lingual enamel surface, and respective lateral enamel surfaces extending between said buccal and lingual enamel surfaces.

17. The method of claim 16 wherein said step of reducing further includes:

producing a plurality of grooves of said selected depth along the ossiferous surfaces targeted for size reduction, said step of producing includes moving said burr end laterally across the ossiferous surfaces being size reduced with resulting penetration of said reduction burr into the ossiferous surfaces being self-limiting by said stop junction disposed against adjacent uncut ossiferous surfaces proximal of the ossiferous surfaces being size reduced; and connecting said plurality of grooves by manipulating said reduction burr laterally over the ossiferous surfaces between respective grooves, thereby reducing the targeted ossiferous surfaces to a depth of reduction provided by said reduction burr length between said stop junction and said distal portion of said burr end.

18. The method of claim 16 wherein said step of reducing further includes:

producing a plurality of grooves of said selected depth along the dental surface targeted for size reduction, said step of producing includes moving said appropriate length of said burr end laterally across the dental surface being size reduced with resulting penetration of said reduction burr into the enamel portions being self-limiting by said stop junction disposed against adjacent enamel portions of the dental surface being size reduced; and connecting said plurality of grooves by manipulating said reduction burr against the enamel portions between each respective groove, thereby reducing the dental surface targeted for reduction to the precise depth of reduction provided by said reduction burr having said appropriate length between said stop junction and said distal burr end.

19. A method of size reduction to precise depths of ossiferous surfaces of a patient's skeleton, comprising the steps of:

providing a reduction burr including an elongated shank extended to a curved shoulder having a cross-section less than said elongated shank, and having an angled stop junction formed by a burr end joined to said curved shoulder, said angled stop junction and said burr end having a sufficiently lesser diameter than said shoulder cross-section thereby providing said angled stop junction for positioning against adjacent ossiferous surfaces for limiting the depth of penetration of said burr end into the ossiferous surfaces;

determining a precise depth of reduction for the ossiferous surfaces;

selecting an appropriate length of said burr end for achieving the precise depth of penetration of said step of determining, said appropriate length being measured from said stop junction at said curved shoulder to a distal portion of said burr end;

manipulating said reduction burr against the ossiferous surfaces with penetration of said reduction burr into the ossiferous surfaces being self-limiting by said stop junction disposed against adjacent uncut ossiferous surfaces, whereby during said step of manipulating, said sufficiently lesser diameter of said stop junction and said burr end allows viewing of said stop junction and periodic viewing of said burr end during said step of manipulating; and cutting the ossiferous surfaces impacted by said distal portion of said burr end for said selected depth in at least one dimension laterally and longitudinally along the ossiferous surfaces targeted for size reduction.

20. The method of claim 19 wherein the ossiferous surfaces of the patient's skeleton are selected from a group consisting of skeletal surfaces proximal of a leg, knee, hip, arm, shoulder, elbow, jaw, and spinal column.

* * * * *